United States Patent [19]

Fields et al.

[11] Patent Number: 4,764,370
[45] Date of Patent: Aug. 16, 1988

[54] VACCINE UTILIZING AN AVIRULENT STRAIN OF *SALMONELLA TYPHIMURIUM*

[75] Inventors: Patricia I. Fields, Cardiff; Constantine G. Haidaris, San Diego; Frederick L. Heffron, Cardiff, all of Calif.

[73] Assignee: Scripps Clinic and Research Foundation, La Jolla, Calif.

[21] Appl. No.: 650,282

[22] Filed: Sep. 12, 1984

[51] Int. Cl.$^4$ .................. C12N 15/00; C12N 1/20; C12N 1/00; A61K 37/00

[52] U.S. Cl. .................. 424/93; 435/172.1; 435/172.3; 435/253; 435/879; 435/317.1; 424/92

[58] Field of Search .......... 435/172.1, 172.3, 253, 435/255, 29, 832, 879, 882, 883, 885, 851, 852, 848, 947, 911, 913, 863, 842, 871, 874; 424/93, 92

[56] References Cited

U.S. PATENT DOCUMENTS 3,855,408 12/1974 Maheswaran .................. 424/92
4,337,314 6/1982 Oeschger et al. ................ 435/253
4,350,684 9/1982 Pardon et al. .................. 424/92
4,440,748 4/1984 Graham ........................ 424/92
4,472,378 9/1987 Shuster et al. .................. 424/92

OTHER PUBLICATIONS

Durland's Medical Dictionary p. 1717 25th Edition W. B. Saunders Publishing Co. 1974.
Yakovleva et al. *Chem. Abst.* vol. 99 1983 p. 202 No. 188723j "Effect of R plasmids in *Salmonella typhimurium* strains of different origin on the vintence of *Salmonellae*.
Hoiseth et al. *Nature* vol. 291 May 21, 1981, pp. 238–239 "Aromatic-dependent *Salmonella typhimurium* are non-virulent and effective as live vaccines".
Grideu et al. *Chem Abst* vol. 99 No. 172722x 1983 p. 367 "Effect of conjugative R plasmids on vintence of antibiotic-sensitive salmonella strains and their streptomyacin sensitive mutants".
Lissner et al. FImm vol. 131(10) pp. 3006–3013 1983 "Genetic control of the innate resistance of mice to *Salmonella typhimurium:* expression of the Itygene in peritoneal and splenic macrophages isolated in vitro".

*Primary Examiner*—Thomas G. Wiseman
*Assistant Examiner*—Robin Lynn Teskin
*Attorney, Agent, or Firm*—Dressler, Goldsmith, Shore, Sutker & Milnamow, Ltd.

[57] ABSTRACT

A vaccine against a microbial pathogen comprised of a live, immunogenic but prototrophic and avirulent mutant strain of the selected microbial pathogen in an amount effective to confer immunity. A method of obtaining a vaccine that induces a heightened cellular and humoral immune response to one of a variety of microbial pathogens in a warm blooded animal. A method for isolation of an avirulent strain of a selected pathogenic microorganism.

4 Claims, No Drawings

VACCINE UTILIZING AN AVIRULENT STRAIN OF *SALMONELLA TYPHIMURIUM*

FIELD OF THE INVENTION

This invention relates to vaccines useful for the prevention or modification of microbial pathogenesis. One aspect of this invention relates to identification and isolation of avirulent mutants of microbial pathogens suitable for such vaccines.

BACKGROUND OF THE INVENTION

The means by which a warm blooded animal overcomes microbial pathogenesis is a complex process. Immunity to microbial pathogenesis is one means by which a warm blooded animal avoids pathogenesis, or suffers a less intense pathogenic state. Incomplete immunity to a given pathogen results in morbidity and mortality in a population exposed to a pathogen.

Achieving an immune state equal to the accelerated secondary immune response following reinfection with a pathogenic microorganism has been a goal of public health officials. This immune response, often achieved only following clinically significant microbial pathogenesis, is sought to be induced by vaccines. Unfortunately, currently available vaccines fall short of this goal. Thus, the accelerated secondary immune response is often found only after the host organism has suffered the disease state.

Vaccines for the purpose of conferring immunity upon a host organism are, of course, known. Vaccines that confer immunity to microbial infections can contain live, attenuated or killed microorganisms, depending upon the type of vaccine. However, the degree of protection conferred by these types of vaccines is highly variable.

It is generally agreed that in the case of intracellular pathogens vaccines based on live but attenuated microorganisms (live vaccines) induce a highly effective type of immune response. Such vaccines have the great advantage that, once the animal host has been vaccinated, entry of the microbial pathogen into the host induces an accelerated recall of earlier, cell-mediated or humoral immunity which is able to control the further growth of the organism before the infection can assume clinically significant proportions. Vaccines based on a killed pathogen (killed vaccine) are generally conceded to be unable to achieve this type of response. However, vaccines that contain a live pathogen present the danger that the vaccinated host upon vaccination may contract the disease against which protection is being sought.

It would be desirable to have a vaccine that possesses the immunizing attributes of a live vaccine but that is not capable of causing an undesirable infection upon vaccination. To this end, a vaccine based on a non-virulent, auxotrophic strain of *Salmonella typhimurium* has been utilized as an experimental immunogen. [Hoiseth et al., Nature 291:238-239 (1981).] However, the described auxotrophic mutant was derived from a model bacteria strain of artificially-maintained virulence, not from a naturally-occurring pathogenic bacteria. In addition, an auxotrophic strain, requiring a metabolite ordinarily unavailable in tissue of the animal to be immunized, may not be able to survive in the animal to be immunized for a time period long enough to induce the desired immunity.

As pointed out hereinabove, microbial agents of disease often present some of the most serious clinical consequences, but only incomplete protection against such agents is provided by currently available vaccines. Furthermore, the lack of reliable in vitro testing in animal models makes it difficult to develop guidelines for the quality control of these vaccines when manufactured in commercial quantities. A method aspect of the present invention mitigates these problems in that a phagocytic cell assay is provided that allows for a relatively easy and reliable identification and selection of microbial strains that are ideal candidates for live vaccines and that confer an adequate level of immunity in the animal sought to be protected. Also, the selected strains are incapable in the first instance of infecting the host with disease-causing pathogens.

Macrophage assays have been used heretofore to determine the sensitivity of macrophages to a given virulent strain of bacteria. [Lissner et al., J. Immun. 131(6):3006-3013 (1983).] Phagocytosis of bacteria by particular types of macrophages has been studied to determine the bactericidal abilities of macrophages from particular subspecies of experimental animals. However, macrophage assays heretofore have not been used to screen for avirulent strains of microbial pathogens.

SUMMARY OF THE INVENTION

This invention, in one aspect, provides a vaccine against a microbial pathogen. This vaccine contains, as its immunogenic agent, a live, prototrophic, but avirulent mutant strain of the microbial pathogen to which an immune reaction is to be induced. The vaccine contains the avirulent mutant strain in an effective amount together with a physiologically tolerable carrier and is free from an infective amount of any virulent strain of the pathogen. The avirulent strain is placed into the vaccine for delivery to a warm blooded animal, in a dosage amount sufficient to confer protection against a virulent strain of the same pathogen. The vaccine embodying this invention can immunize against a pathogenic microbe such as a bacteria, a protozoa, and a fungus.

Another aspect of this invention provides a method for obtaining an avirulent strain suitable for use in the aforesaid vaccine. This method entails providing a population of a virulent strain of the selected pathogen, which can be a pathogenic bacteria, protozoa or fungus. A portion of the virulent strain population is subjected to a known mutation-inducing condition for such a time period as will induce mutation in that population. One or more of pathogens subjected to a mutation-inducing condition is then cloned to provide a genetically homologous population in each case.

The cloned population is assayed for avirulence by providing an aliquot of phagocytic cells from a warm blooded animal and infecting those cells with an aliquot of the virulent population of the pathogen for a control. A similar aliquot of phagocytic cells is infected with an aliquot of the cloned population that has been subjected to mutation-inducing conditions.

The infected phagocytic cell aliquots are incubated for at least twenty-four hours, and a determination is made at predetermined interval or intervals during the incubation period of the number of pathogens present in the aliquots undergoing incubation. The assayed cloned population exhibiting at least a 10 percent decrease in the sum of the average number of cloned pathogens per phagocyte per unit of time over the twenty-four hour incubation period, as compared to the incubated control aliquot, is retained for vaccine production. Preferably, the avirulent strain retained for vaccine production exhibits at least a 50 percent decrease in the sum of the average number of cloned pathogens per phagocyte per unit of time over the twenty-four hour incubation period. Illustrative types of phagocytic cell that can be used for this purpose are macrophage and polymorphonuclear leucocyte.

If desired, the cloned population is further tested for avirulence by introduction of the retained avirulent mutant strain into a warm blooded animal.

DETAILED DESCRIPTION OF THE INVENTION

As used herein and in the appended claims, the following definitions apply.

ATCC Number—a designation of the American Type Culture Collection (Rockville, Md.) for microorganisms deposited at the foregoing institution.

Auxotrophic—a strain requiring a growth factor not required by the parental or prototype strain.

Chromosome—a discrete unit of a genome carrying many genes and coded on a DNA molecule.

Clone—a group of cells descended from a single common ancestor, thereby having an identical genotype.

DNA Sequence—A linear series of nucleotides connected to one another by phosphodiester bonds between the 3′ and 5′ carbons of adjacent pentoses.

Genotype—the genetic constitution of an organism.

Immunity—the ability to raise antibodies to a particular pathogen and/or elicit a cellular immune response.

$LD_{50}$ or Lethal Dose 50—that amount of a pathogen that will kill 50 percent of a population of organisms within a given period of time.

Macrophage—any mononuclear phagocytic cell that occurs in the walls of blood vessels in loose connective tissue and in the organs of the reticuloendothelial system of a warm blooded animal.

Microorganism—a minute living organism, usually microscopic, such as bacteria, yeasts, molds and protozoa.

Mutagen—a reagent that increases the rate of mutation by causing changes in DNA.

Mutation—an inheritable change in a chromosome.

Phagocyte—any cell that ingests microorganisms or other cells and foreign particles, e.g., macrophage, polymorphonuclear leucocyte, and the like.

Phenotype—the characteristic of an organism resulting from the interaction of its genetic constitution with the environment.

Prototrophic—having the same growth factor requirements as the ancestral, parent, or prototype nonmutant strain.

Transposon—a DNA sequence able to replicate and insert one copy thereof at a new location in the genome.

To produce the present vaccines, a naturally-occurring virulent pathogen is subjected to conditions capable of producing an avirulent strain of the same pathogen. The avirulent strain is identified and cloned, and an effective amount of the avirulent strain is combined with a suitable, physiologically tolerable carrier, e.g., with a liquid such as physiological saline, phosphate-buffered saline (PBS), or other ingestable or injectable liquid, enteric tablet or capsule, a suppository, or the like. To confer immunity, an effective amount of the avirulent strain so formulated is introduced into the animal to be immunized in one or more serially administered doses. For optimum immunity it is preferred to administer a series of doses over a period of time. Administration of the avirulent strain can be effected by injection, usually intramuscularly or subcutaneously, orally by ingesting a tablet or capsule, as a suppository, as a nasal spray, or by any other suitable route of administration.

For a warm blooded animal, a suitable dose depends, in part, upon the chosen route of administration and a number of other factors. Included among those factors are the body weight of the recipient to be immunized, the carrier when used, and the number of inoculations desired to be used.

Individual inoculations typically contain unit doses of about 10 micrograms to about 100 milligrams of the live avirulent strain, exclusive of any carrier that may be present. In any event, the immunogen contained in the vaccine is present in an "effective amount," which amount in a particular instance depends upon a variety of factors as is well known in the immunological arts and as discussed above.

Once a pathogenic organism is selected for transformation into an avirulent strain, the desired mutagenesis can be achieved by one of several methods. In particular, mutagenesis may be induced by one of several means. The method of mutagenesis applied depends on the organism subjected to the procedure. Generally it is preferred that the mutation be as localized as possible and further that the reversion to the original genotype of the pathogen be as limited as possible. The several methods of mutagenesis that may be applicable include chemically induced mutation, radiation induced mutation as well as mutagenesis by DNA insertion.

Mutagenesis by DNA insertion may be accomplished by transposon mutagenesis. This is a relatively non-reverting mutation accomplished at a localized site in the chromosome. Transposon mutagenesis results in the appearance of a linear segment of DNA, already contained in a cell, at a second site in the DNA molecule of the same cell.

Controlled, site-directed mutagenesis is accomplished by replacing a native gene in the microorganism with a gene containing a defined mutation. This method is particularly applicable to microorganisms of the genera Salmonella, Streptococcus and Neisseria, and to some fungi.

Uncontrolled random mutagenesis is accomplished by exposing the selected organism to a chemical mutagen or to a radioactive mutagen. Uncontrolled random mutagenesis is the only method of inducing mutations in protozoa parasites known at this time. The procedure is limited in applicability because the resulting genetic lesion cannot be easily localized, nor is there a genetic tag for the strain. The genetic lesion may also easily revert to the parent genotype.

The avirulence of a produced strain is determined by assaying that strain for its inability to proliferate or survive in the presence of phagocytic cells. In a preferred embodiment of this invention, peritoneal macrophages of a warm blooded animal are the phagocytic cells used for assay. Other types of phagocytic cells can be used, however.

The survival of the strain in question within the phagocytes indicates virulence or avirulence. If the strain is virulent, the number of cells of the strain being assayed generally increase within the macrophage culture over a period of time. On the other hand, the number of cells of the strain being assayed generally decrease within the macrophage culture over a period of time if the strain is avirulent.

The present utilization of the assay permits the analysis of the interaction between the microbe and the phagocyte in discrete steps. The assay can be used to analyze the attachment to and the entry of the cells of the strain into the phagocyte. The intracellular fate of the cells of the strain within the phagocyte can also be analyzed.

The assay is conducted by performing the following steps. A known virulent strain of a microbial pathogen to which immunity is sought in a host organism is selected. A population of the known virulent pathogen is obtained. A portion of the population of known virulent pathogen is subjected to a mutation inducing condition for a time period sufficient to induce a mutation. A genetically identical population of the mutated strain is then cloned.

A portion of the cloned mutated population is treated by infecting an aliquot of phagocytic cells with an aliquot of the mutated strain population. In a like manner, an aliquot of phagocytic cells is infected with an aliquot of the known virulent strain. The infected phagocytic cell populations are incubated for at least twenty-four hours. At a predetermined interval or intervals during the incubation, the respective numbers of a mutated strain population and known virulent pathogens present in the incubated aliquots are determined.

This particular determination can be carried out in several ways, depending upon the nature of the involved microbes. One such method entails washing the incubated phagocytic cells to remove extraneous matter, lysing the phagocytes but not the involved microbes, and counting the number of microbes that are present. A suitable phagocyte lysing solution in the case of macrophages is sodium deoxycholate in PBS, which solution can be used in instances where the involved microbes are not adversely affected thereby.

If, on the other hand, the phagocyte lysing solution does adversely affect the microbes that are to be counted, the number of microbes present is ascertained using radiolabeling, enzyme-linked immunoassay (ELISA), radioimmunoassay (RIA), Giemsa staining techniques, or like expedients. In particular, the microbe may be labelled with a radioactive nucleic acid precursor (e.g., tritiated thymidine) and the amount of labelled precursor incorporated into the nucleic acid of the microbe can be quantitated. The number of microbes associated with the phagocytes thus can be determined by labelling the microbe with the radiolabelled nucleic acid precursor prior to incubation with the phagocytes. After washing away the unphagocytized microbes, the acid-precipitable or water-insoluble radioactive moieties associated with the phagocyte monolayer can be determined by collecting the infected phagocytes and subjecting the infected phagocytes to liquid scintillation counting or gamma radiation counting. The counts per minute obtained are directly proportional to the number of microbes associated with the phagocyte monolayer.

Alternatively, after washing away unphagocytized microbes using PBS, the infected monolayers can be fixed to the bottom of the microtiter well using a suitable fixative such as methanol. An aliquot of antiserum previously raised against the microbe is admixed with the fixed infected phagocyte monolayer in the microtiter well. The resulting admixture is then incubated at 4° C. for at least 2 hours. Thereafter, unbound antibody present in the incubated admixture is washed away using PBS. The antibody bound to the phagocytes in the microtiter well can then be quantitated using RIA or ELISA procedures. The amount of specific antibody bound is proportional to the number of microbes phagocytized.

Yet another alternative is to visualize after washing away unphagocytized microbes, the number of microbes associated with the phagocyte monolayer in the microtiter well by staining the microbes using Giemsa stain and counting the stained microbes using light microscopy. Using this particular protocol, the percent of infected cells and the average number of microbes associated with each phagocyte can be determined.

The cloned population of the mutated strain is retained where the mutated strain exhibits at least a 10 percent decrease, preferably at least a 50 percent decrease, in the sum of the average number of mutated strain cloned pathogens per unit time over the time period of the assay, i.e., twenty-four hours, as compared to the incubated aliquot where known virulent pathogens are present.

The retained cloned population is deemed to be avirulent where it meets the above criteria and thus is suitable for incorporation into a vaccine which is prepared by further cloning of the retained population so as to produce a desired quantity of the avirulent strain in a substantially pure form and then combining a predetermined population of the avirulent strain with a physiologically tolerable carrier at a predetermined concentration.

For any microbe to be tested, the assay involves the interaction of the microbe with phagocytes from a suitable host in vitro. For optimum results, the interpretation of the experimental data and the establishment of the criterion of avirulence is to be tailored for the specific genus and specie of the microbe that is a candidate for a vaccine, and allowance is made for the way that this particular organism interferes with normal phagocyte function. For example, if a specific microorganism is rapidly killed upon ingestion by macrophages, but is able to interfere with normal phagocyte function by avoiding phagocytosis, then one screens mutants in the assay as described above, but selects mutants that have been ingested by macrophages in significantly higher amounts as compared to the parent strain. If the particular organism interferes with normal phagocyte function by its ability to survive or multiply within the phagocyte, then one screens for mutants that were unable to grow or survive within the phagocyte.

Mutants that are identified as being avirulent can be further tested for avirulence by a second, confirming criterion—the reduced capacity of the mutant to kill a suitable animal host as compared to the corresponding virulent strain.

Those mutants that are determined to be avirulent as compared to the parental strain on the basis of the in vitro and optional in vivo assays can then be further tested for their ability to confer protection against challenge with the parental strain by immunizing the host with the mutant strain prior to exposure of the host to the virulent parent strain. Protection is defined as the ability of the host animal to survive the challenge of a lethal dose of the virulent parent strain after immunization with the mutant.

The foregoing procedures of mutant isolation, screening in vitro and in vivo, and immunization with the selected mutants, provide means by which avirulent strains of pathogenic microorganisms are obtained that are suitable for use in vaccines.

Vaccines can be prepared in the foregoing manner against pathogenic strains of bacteria, protozoa and yeast. With respect to bacteria, illustrative vaccines are those derived from avirulent strains of Staphylococcus, e.g., Staphylococcus aureus, Salmonella, e.g., Salmonella typhimurium, Streptococcus, Haemophilus, Klebsiella, Escherichia, Treponema, Mycobacterium, Chlamydia, Rickettsia, Listeria, Bacillus, Yersinia, Brucella, Legionella, Shigella, Clostridium, Neisseria and Pseudomonas.

With respect to protozoa, illustrative vaccines are those derived from avirulent strains of Toxoplasma, Trypanosoma, Plasmodium, Leishmania and Entamoeba.

With respect to fungi, illustrative vaccines are those derived from avirulent strains of Cryptococcus and Aspergillus.

EXAMPLE 1

Preparation of Vaccines Against Salmonella

Materials and Methods

Salmonella typhimurium (S. typhimurium) ATCC 14028 was selected as the pathogen. The selected pathogen was then subjected to a macrophage assay procedure, an avirulent strain was isolated, and a vaccine was formulated utilizing the isolated avirulent strain.

BALB/C mice (Scripps Clinic and Research Foundation Vivarium, La Jolla, Ca.) were selected as the experimental animals of choice because of their sensitivity to S. typhimurium ATCC 14028. The $LD_{50}$ for BALB/C was determined to be less than 10 organisms per mouse when injected into the peritoneum of the mouse.

S. typhimurium ATCC 14028 was found to be prototrophic. This was determined by evaluating the growth of the microorganisms on minimal glucose media containing the M9 salts and 0.5 percent glucose.

S. typhimurium ATCC 14028 was also found to be sensitive to several antibiotics. This was determined by plating the known virulent strain onto media containing 20 micrograms per milliliter tetracycline. Sensitivity to the other antibiotics was determined by plating the bacteria onto individual media containing 30 micrograms per milliliter chloramphenicol, 50 micrograms per milliliter ampicillin, 100 micrograms per milliliter streptomycin or 20 micrograms per milliliter kanamycin, respectively. Antibiotic sensitivity was determined using LB Medium (Sigma, St. Louis, MO) and a selected antibiotic in the above disclosed amounts.

Media utilized in the assay was formulated in accordance with the following recipes.

| LB Medium | |
|---|---|
| 10 grams | Bacto-tryptone |
| 5 grams | Bacto-yeast extract |
| 10 grams | NaCl |
| 1 liter | $H_2O$ |
| pH adjusted to approximately 7.0 for solid media, 15 grams agar per liter added | |

| Minimal Medium | | |
|---|---|---|
| 6 grams | $Na_2HPO_4$ | |
| 3 grams | $KH_2PO_4$ | |
| 0.5 grams | NaCl | |
| 1 gram | $NH_4Cl$ | "M9 Salts" |
| 100 micromole | $CaCl_2$ | |
| 1 micromole | $MgSO_4$ | |
| supplemented with 0.5% lactose or 0.5% glucose and 50 micromoles thiamine | | |

Primary Plating Media

The media listed in this section were used in petri dishes for initial isolation. The composition of the medium was such that it was selective for the particular group of organisms of interest.

| Bacto MacConkey Agar (B75) Dehydrated | |
|---|---|
| Bacto-Peptone | 17 grams |
| Proteose Peptone, Difco | 3 grams |
| Bacto-Lactose | 10 grams |
| Bacto-Bile Salts No. 3 | 1.5 grams |
| Sodium Chloride | 5 grams |
| Bacto-Agar | 13.5 grams |
| Bacto-Neutral Red | 0.03 grams |
| Bacto-Crystal Violet | 0.001 grams |
| Supplemented with appropriate amount of antibiotics for antibiotic sensitivity | |
| Added to 1 liter $H_2O$ | |

Mutagenesis

Transposon Tn10 derived from strain TT627 [Chuley et al., Genet. 91:639-655] was inserted into the genetic material of the selected S. typhimurium ATCC 14028.

TT627 contains a conjugative F' factor which is able to be passed from one cell to another. TT627 is temperature sensitive and will replicate at 30° C., but not at 42° C. The F' factor is an extrachromosomal circular DNA, or plasmid, that also carries lactose utilization functions from E. coli and Tn10 (a transposon conferring tetracycline resistance).

TT627 and S. typhimurium ATCC 14028 were grown at 30° C. to mid-logarithmic phase in LB broth (a rich, complex media) and then mixed at a ratio of 1:1. The two strains were incubated together for 1 hour. During this period conjugation between the two strains will transfer the corresponding F' plasmid from TT627 to S. typhimurium ATCC 14028. The incubated cells were then pelleted by centrifugation, washed in minimal media, placed on minimal lactose media containing tetracycline and grown for 36 hours at 30° C. S. typhimurium ATCC 14028 is naturally unable to ferment lactose, therefore, S. typhimurium ATCC 14028 will only grow on this media if it has received the plasmid. TT627 will not grow on this media, since it requires uracil for growth (which has omitted from the media). Thus, the only bacteria that should grow on this media are the "transconjugants," S. typhimurium ATCC 14028 carrying the F' plasmid.

The presence of the transconjugant was then confirmed by its metabolic characteristics. The transconjugant was found to be prototrophic. The transconjugant was tetracycline resistant and able to ferment lactose.

Single colonies of this transconjugant isolate were grown at 30° C. They were then streaked on differential media containing tetracycline and lactose, and incubated at 42° C. Colonies that were unable to ferment lactose were white, colonies fermenting lactose were pink. A single white colony was picked from each streak. The appearance of the white colony indicated it was not fermenting lactose, indicating that it has lost the F' plasmid. The chosen colony was tetracycline resistant indicating it had retained the transposon by transposition to the genome. These mutants were then screened in the in vitro macrophage assay for avirulence.

The Assay

Mouse-elicited peritoneal exudate cells served as macrophage source. These cells were seeded into a 96 well microtiter dish (Corning, Corning, N.Y.) and the macrophages, approximately $10^5$/well, were allowed to adhere. Nonadherent cells were washed off and the bacteria, one clonal colony population per well, were added at a ratio of one bacteria to one macrophage. The infected macrophages were incubated one hour to allow time for phagocytosis of the bacteria. Non-phagocytized bacteria were then inactivated by the addition of gentamicin at a concentration of 200 micrograms per milliliter. After two hours the macrophages were washed to remove dead extracellular bacteria, and the washed macrophages were incubated for an additional 24 hours. At that point the macrophages were lysed by removing the media and replacing it with a macrophage lysing solution of 0.5 percent sodium deoxycholate (Sigma) in PBS. The number of viable intracellular bacteria were determined by plating an aliquot from each well of the microtiter plate onto LB agar. After incubation for 18 hours, growth of the number of surviving bacteria was determined by counting the number of colonies on each plate. Avirulent strains of S. typhimurium ATCC 14028 exhibited about 10- to 20-fold lower number of viable intracellular bacteria than the virulent S. typhimurium ATCC 14028 strains after 24 hour incubation with macrophages in the above described assay. A number of mutants of S. typhimurium ATCC 14028 have been identified by this procedure and confirmed by a further assay in which peritoneal macrophages from BALB/C mice were used.

The mouse peritoneal macrophages were elicited by intraperitoneal (i.p.) injection of 3% thioglycollate broth (Gibco, Grand Island, N.Y.) four days before harvesting. This treatment stimulated macrophage migration into the peritoneum. Macrophage recovery was increased without a concurrent stimulation of the macrophages to increased bacteriocidal activity. Elicited macrophages were harvested by intraperitoneal injection 5.0 ml Hanks Balanced Salt Solution (HBSS) (Gibco), massaging the peritoneum, and recovering the injected HBSS. The cells recovered were washed, resuspended in Dulbecco's Modified Eagle Medium (DMEM) (Gibco) with 10 percent fetal calf serum and 100 micrograms gentamicin/ml (Sigma, St. Louis) and seeded in a 96-well microtiter plate (Corning, Corning, N.Y.) at about $2\times10^5$ cells per well.

Approximately half of the peritoneal exudate cells (PEC's) obtained in accordance with the above described procedure are macrophages. Macrophages were easily separated from the peritoneal exudate by adherence to the microtiter well. After two hours incubation at 37° C. with 5 percent carbon dioxide in air, nonadherent cells were washed off, the media replaced, and the plates were incubated eighteen hours before use.

The obtained macrophage monolayers were then washed to remove antibiotics. Approximately $10^5$ of the mutant strain of bacteria were added to each well in 50 microliters DMEM plus 10 percent Fetal Calf Serum (FCS) (Gibco).

Control wells, containing the parent strain, were prepared in a manner identical to that used for the mutant strain plate. Approximately $10^5$ of the virulent parent strain were added to each well in 50 microliters DMEM plus 10 percent FCS was added to each parent strain well.

To permit phagocytosis the macrophages were incubated with the pathogen strain one hour at 37 degrees C., with 5 percent $CO_2$ in air. After one hour 200 microliters of DMEM with FCS containing 200 micrograms gentamicin/ml was then added to inactivate extracellular bacteria, and the plates were incubated 2 hours.

The media was then removed from the wells and replaced with 200 microliters DMEM containing 10 percent FCS and 10 micrograms gentamicin/ml. The plates were then incubated 20-24 additional hours. At that time, intracellular survival of the mutants was assessed.

The media was removed from the wells and replaced with 200 microliters 0.5 percent sodium deoxycholate in normal saline. This treatment lysed the macrophage within a few minutes. The content of each well was then thoroughly mixed, and an aliquot of the contents of each well spread on a separate LB plate. The plates were incubated overnight at 37° C.

The number of colonies on the plates inocculated from the wells containing the mutants was compared to the number of colonies from the wells containing the parent, virulent strain. Plates containing at least twofold less colonies than the control plates were selected as avirulent mutants. These were retested in accordance with the in vitro assay protocol, to confirm avirulence. A further confirmation of avirulence was made by injection into BALB/C mice.

Confirmation/Analysis of Avirulent Mutants

Overnight cultures of the putative avirulent mutants were diluted in phosphate buffered saline (PBS) and approximately 500 organisms injected i.p. into BALB/c mice. This dose is equivalent to 50 $LD_{50}$ for the virulent strain. 50 $LD_{50}$ of the parent virulent strain killed all mice receiving that dose in preliminary experiments. The mice receiving avirulent strains survived 3 weeks, confirming avirulence of the mutants.

To date approximately 3000 mutants have been screened using methods set forth herein. Thirty-four putative mutants have been isolated. Twenty-one of these mutants have been tested in mice by injection of 50 $LD_{50}$ of virulent pathogens of the organism into each of two BALB/C mice. In these tests, it is normally seen that within seven days of the injection the virulent parent strain at 50 $LD_{50}$ results in death. As is seen in Table I immediately following, 12 mice inoculated with the avirulent mutant strain vaccine showed complete resistance to the dosage of 50 $LD_{50}$ virulent parent pathogen. Nine mice showed some sensitivity to that dose, either becoming sick and recovering or becoming sick and dying.

Generally, however, mice injected with the avirulent pathogen vaccine survived longer than mice receiving the virulent pathogen.

Of twelve mice that were inoculated with the avirulent mutant strain vaccine and survived four groups of two mice each have been challenged with parent strain. This challenge was conducted by injecting $10^6$ virulent parent strain organisms (100,000 $LD_{50}$) into the mice. Three of the four groups of mice so challenged were completely protected, i.e. survived the challenge with the $^6$ organisms. Control animals receiving no vaccine, injected with $^{6}$ organisms of the virulent parent strain died within seven days.

Mice were challenged with various multiples of the $LD_{50}$ using avirulent mutants of normally virulent strains. Avirulent strains, determined by the macrophage assay were introduced into the mice at 50 $LD_{50}$ determined virulent parent strains. Table I below indicates the survival rate of these mice so challenged.

TABLE I

| ATCC No. | Mutant Strain No. | Challenge of Experimental Animals With Avirulent Mutant, and Protection Assay: Number of Mice Challenged | Challenge With Avirulent Mutant Survival at dose of 50 $LD_{50}$ | Challenge With Avirulent Mutant Survival at dose of 1000 $LD_{50}$ | Protection Assay Survival after Vaccination With 50 $LD_{50}$ and Challenge w/100,000 $LD_{50}$ |
|---|---|---|---|---|---|
| 39848 | 1 SCRF 60.0 | 2 | + | + | + |
| 39849 | 2 SCRF 60.0 | 2 | + | + | + |
| 39847 | 4 SCRF 60.0 | 2 | + | + | + |
| | 3 SCRF 60.0 | 2 | + | + | − |
| | 2-90 SCRF 60.0 | 2 | + | NT | ± |
| | 3-17 SCRF 60.0 | 2 | − | NT | NT |
| | 8-27 SCRF 60.0 | 2 | ± | NT | NT |
| | 8-79 SCRF 60.0 | 2 | + | NT | ± |
| | 9-41 SCRF 60.0 | 2 | ± | NT | NT |
| | 9-49 SCRF 60.0 | 2 | ± | NT | NT |
| | 10-98 SCRF 60.0 | 2 | ± | NT | NT |
| | 12-20 SCRF 60.0 | 2 | − | NT | NT |
| | 13-15 SCRF 60.0 | 2 | − | NT | NT |
| | 13-21 SCRF 60.0 | 2 | dnc | NT | NT |
| | 13-52 SCRF 60.0 | 2 | dnc | NT | NT |
| | 14-5 SCRF 60.0 | 2 | + | NT | ± |
| | 14-13 SCRF 60.0 | 2 | dnc | NT | NT |
| | 14-46 SCRF 60.0 | 2 | dnc | NT | NT |
| | 15-21 SCRF 60.0 | 2 | + | NT | − |
| | 15-23 SCRF 60.0 | 2 | + | NT | − |
| | 15-92 SCRF 60.0 | 2 | ± | NT | NT |
| | 16-1 SCRF 60.0 | 2 | + | NT | − |
| | 16-33 SCRF 60.0 | 2 | + | NT | ± |
| | 16-48 SCRF 60.0 | 2 | dnc | NT | NT |
| | 16-54 SCRF 60.0 | 2 | dnc | NT | NT |
| | 16-68 SCRF 60.0 | 2 | dnc | NT | NT |
| | 18-96 SCRF 60.0 | 2 | ± | NT | NT |
| | 19-96 SCRF 60.0 | 2 | + | NT | ± |
| | 20-27 SCRF 60.0 | 2 | dnc | NT | NT |
| | 21-13 SCRF 60.0 | 2 | − | NT | NT |
| | 22-21 SCRF 60.0 | 2 | ± | NT | NT |
| | 23-18 SCRF 60.0 | 2 | ± | NT | NT |
| | 24-67 SCRF 60.0 | 2 | ± | NT | NT |
| | 26-6 SCRF 60.0 | 2 | dnc | NT | NT |

NT = Not tested
\+ = both mice survived with no obvious disease
± = one mouse died or one or more sick and not yet recovered
dnc = data not collected It is readily seen from the above Table that mice challenged with multiples of the $LD_{50}$ of virulent parent strains survived following the innoculation with the vaccine containing 500 avirulent bacteria.

EXAMPLE 2

In a manner similar to Example 1 the avirulence of a mutant strain of Staphylococcus is determined. A particular virulent strain of the genus Staphylococcus is selected. Phagocytes sensitive to the particular selected specie of the genus Staphylococcus are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Staphylococcus is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 3

In a manner similar to Example 1 the avirulence of a mutant strain of *Staphylococcus aureus* is determined. A particular virulent strain of *Staphylococcus aureus* is selected. Phagocytes sensitive to the particular selected specie of *Staphylococcus aureus* are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from *Staphylococcus aureus* is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 4

In a manner similar to Example 1 the avirulence of a mutant strain of Streptococcus is determined. A particular virulent strain of the genus Streptococcus is selected. Phagocytes sensitive to the particular selected specie of the genus Streptococcus are selected by screening strains of a warm blooded animal, e.g., mouse, for sensitivity.

Phagocytes are harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function.

The virulent parent strain of the specie selected from the genus Streptococcus is assayed using phagocytes and the number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 5

In a manner similar to Example 1 the avirulence of a mutant strain of Haemophilus is determined. A particular virulent strain of the genus Haemophilus is selected. Phagocytes sensitive to the particular selected specie of the genus Haemophilus are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population by a chemical agent.

A member of the mutant population is selected and tested for its inability to interfere with normal phagocyte function.

The virulent parent strain of the specie selected from the genus Haemophilus is assayed using phagocytes and the number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 6

In a manner similar to Example 1 the avirulence of a mutant strain of Klebsiella is determined. A particular virulent strain of the genus Klebsiella is selected. Phagocytes sensitive to the particular selected specie of the genus Klebsiella are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Klebsiella is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 7

In a manner similar to Example 1 the avirulence of a mutant strain of Escherichia is determined. A particular virulent strain of the genus Escherichia is selected. Phagocytes sensitive to the particular selected specie of the genus Escherichia are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Escherichia is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 8

In a manner similar to Example 1 the avirulence of a mutant strain of Listeria is determined. A particular virulent strain of the genus Listeria is selected. Phagocytes sensitive to the particular selected specie of the genus Listeria are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Listeria is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 9

In a manner similar to Example 1 the avirulence of a mutant strain of Bacillus is determined. A particular virulent strain of the genus Bacillus is selected. Phagocytes sensitive to the particular selected specie of the genus Bacillus are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Bacillus is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 10

In a manner similar to Example 1 the avirulence of a mutant strain of Yersinia is determined. A particular virulent strain of the genus Yersinia is selected. Phagocytes sensitive to the particular selected specie of the genus Yersinia are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Yersinia is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 11

In a manner similar to Example 1 the avirulence of a mutant strain of Brucella is determined. A particular virulent strain of the genus Brucella is selected. Phagocytes sensitive to the particular selected specie of the genus Brucella are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population by radiation.

A member of the mutant population is selected and tested for its inability to interfere with normal phagocyte function.

The virulent parent strain of the specie selected from the genus Brucella is assayed using phagocytes and the number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 12

In a manner similar to Example 1 the avirulence of a mutant strain of Legionella is determined. A particular virulent strain of the genus Legionella is selected. Phagocytes sensitive to the particular selected specie of the genus Legionella are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population by radiation.

A member of the mutant population is selected and tested for its inability to interfere with normal phagocyte function.

The virulent parent strain of the specie selected from the genus Legionella is assayed using phagocytes and the number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 13

In a manner similar to Example 1 the avirulence of a mutant strain of Shigella is determined. A particular virulent strain of the genus Shigella is selected. Phagocytes sensitive to the particular selected specie of the genus Shigella are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Shigella is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 14

In a manner similar to Example 1 the avirulence of a mutant strain of Pseudomonas is determined. A particular virulent strain of the genus Pseudomonas is selected. Phagocytes sensitive to the particular selected specie of the genus Pseudomonas are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population in a manner similar to Example 1.

A member of the mutant population is selected and tested for its inability to interfere with normal phagocyte function in a manner similar to Example 1 described above.

The virulent parent strain of the specie selected from the genus Pseudomonas is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

EXAMPLE 15

In a manner similar to Example 1 the avirulence of a mutant strain of Salmonella is determined. A particular virulent strain of the genus Salmonella is selected. Phagocytes sensitive to the particular selected specie of the genus Salmonella are selected by screening strains of a warm blooded animal, e.g., mouse, for sensitivity.

Phagocytes are then harvested from the warm blooded animal strain exhibiting the desired sensitivity.

Mutations are induced in a portion of the virulent pathogen population. Mutation may be induced by transposon in a similar manner to Example 1.

A member of the mutant population is selected and tested for its inability to interfere with normal phagocyte function in a manner similar to Example 1 described above.

The virulent parent strain of the specie selected from the genus Salmonella is assayed as described in Example 1. The number of pathogens surviving in the phagocyte assay is determined.

Upon determining an avirulent strain of a selected virulent pathogen, a population of the avirulent strain is cloned. An aliquot of the avirulent strain in conjunction with a physiologically tolerable carrier is then introduced at least once, preferably on several occasions, into the animal to be protected to confer immunity. The dose of the vaccine depends upon the particular pathogen assayed, the vehicle employed for inoculation, the degree of immunity sought and the frequency of administration of the vaccine.

The foregoing specification, including the examples, is intended to be illustrative and is not to be taken as limiting. Still other variations within the spirit and scope of this invention are possible and will present themselves to those skilled in the art.

What is claimed is:

1. A method of immunizing a warm blooded animal against a microbial pathogen comprising the steps of:

(a) selecting at least one live, immunogenic but prototrophic and avirulent mutant strain selected from the group consisting of *S. typhimurium* strains ATCC 39847, ATCC 39848 and ATCC 39849, and a physiologically tolerable carrier therefor; and (b) administering an amount of the selected avirulent mutant strain to the animal sufficient to induce immunity in said animal.

2. The avivulent, prototrophic, tetracycline resistant transponson Tn10 containing *Salmonella typhimurium* vaccine strain designated ATCC 39847.

3. The avirulent, prototrophic, tetracycline resistant, transposon Tn10 containing *Salmonella typhimurium* vaccine strain designated ATCC 39848.

4. The avirulent, prototrophic, tetracycline resistant, transposon Tn10 containing *Salmonella typhimurium* vaccine strain designated ATCC 39849.

* * * * *

UNITED STATES PATENT AND TRADEMARK OFFICE
CERTIFICATE OF CORRECTION

PATENT NO.   : 4,764,370
DATED        : August 16, 1988
INVENTOR(S)  : Patricia L. Fields et al.

It is certified that error appears in the above-identified patent and that said Letters Patent is hereby corrected as shown below:

Column 1, after the heading "DESCRIPTION" and before the heading "TECHNICAL FIELD", insert the following paragraph:

--This invention was made with government support under Contract AI 20978 awarded by the National Institutes of Health. The government has certain rights in the invention.--

Signed and Sealed this

Eleventh Day of January, 1994

Attest:

BRUCE LEHMAN

*Attesting Officer*        *Commissioner of Patents and Trademarks*